US008529909B2

(12) United States Patent

Rapak et al.

(10) Patent No.: US 8,529,909 B2
(45) Date of Patent: Sep. 10, 2013

(54) METHOD FOR THE PRODUCTION AND PURIFICATION OF BOVINE LEUKEMIA VIRUS GP51 SURFACE GLYCOPROTEIN IN THE ABSENCE OF BOVINE SERUM

(75) Inventors: Andrzej Rapak, Wroclaw (PL); Ewa Ziolo, Wroclaw (PL)

(73) Assignee: Instytut Immunologii I Terapii, Wroclaw (PL)

( * ) Notice: Subject to any disclaimer, the term of this patent is extended or adjusted under 35 U.S.C. 154(b) by 0 days.

(21) Appl. No.: 13/059,568

(22) PCT Filed: Sep. 27, 2009

(86) PCT No.: PCT/PL2009/050027

§ 371 (c)(1), (2), (4) Date: Jun. 15, 2011

(87) PCT Pub. No.: WO2010/036134

PCT Pub. Date: Apr. 1, 2010

(65) Prior Publication Data

US 2011/0250624 A1 Oct. 13, 2011

(30) Foreign Application Priority Data

Sep. 29, 2008 (PL) ........................................ 386176

(51) Int. Cl.
*A61K 39/21* (2006.01)
*C07K 1/00* (2006.01)

(52) U.S. Cl.
USPC ........................................ 424/207.1; 530/416

(58) Field of Classification Search
None
See application file for complete search history.

(56) References Cited

U.S. PATENT DOCUMENTS

| | | | | |
|---|---|---|---|---|
| 7,432,101 | B2 * | 10/2008 | Guehenneux et al. | 435/235.1 |
| 2009/0017517 | A1 * | 1/2009 | Schickli et al. | 435/173.6 |

OTHER PUBLICATIONS

De Giuseppe, A., et al., Jan. 2004, Expression of the bovine leukemia virus envelope glycoprotein (gp51) by recombinant baculovirus and its use in an enzyme-linked immunosorbent assay, Clin. Diag. Lab. Immunol. 11(1):147-151.*

Merza, M., et al., Aug. 1991, Immunoaffinity purification of two major proteins of bovine leukemia virus (gp51 and p24) and their use for discrimination between vaccinated and infected animals, J. Virol. Methods 33(3):345-353 (abstract only).*

Gibco Invitrogen Cell Culture Optipro SFM, May 2006, Form No. 3943.*

International Search Report issued by the International Searching Authority (ISA/O . E. P . M. ) on Jan. 29, 2010 in connection with International Application No. PCT/PL2009/050027.

* cited by examiner

*Primary Examiner* — Jeffrey S. Parkin

(74) *Attorney, Agent, or Firm* — Gary J. Gershik; Cooper & Dunham LLP

(57) ABSTRACT

The subject of the present invention is a method of obtaining purified BLV gp51 antigen as well as a novel ELISA assay using said antigen. The present invention is useful in the diagnosis of enzootic leukaemia in cattle.

5 Claims, No Drawings

METHOD FOR THE PRODUCTION AND PURIFICATION OF BOVINE LEUKEMIA VIRUS GP51 SURFACE GLYCOPROTEIN IN THE ABSENCE OF BOVINE SERUM

This application is a §371 national stage entry of PCT International Application No. PCT/PL2009/050027, filed Sep. 27, 2009, claiming priority of Polish Application No. PL386176, filed Sep. 29, 2008, the entire contents of each of which are hereby incorporated by reference.

FIELD OF THE INVENTION

The subject of the present invention is a method of obtaining purified BLV gp51 antigen as well as a novel ELISA assay using said antigen. The present invention is useful in the diagnosis of enzootic leukemia in cattle.

BACKGROUND OF THE INVENTION

Enzootic bovine leukemia (EBL) is an infectious disease of cattle caused by a type C retrovirus, BLV (Bovine Leukemia Virus) and consists of lymphatic node hypertrophy. The disease is characterized by a long incubation period (up to 7 years) and, in most cases, (ca. 60%) proceeds without symptoms. Lymphatic cysts form in a portion of adult cattle (10-30%), whereas 1-10% develop lymphatic sarcomas on various internal organs, with a marked increase of B lymphocytes.

A strong immune response occurs in infected individuals, which is used in serological diagnostics. Despite the fact that the titer of anti-BLV antibodies increases as the disease progresses, they are not able to halt the infection. Because the disease develops asymptomatically through a long initial phase, the only effective method of preventing transmission are frequent serological diagnostics and the elimination of infected animals. Serological assays are performed on animals over 6 months, when maternal antibodies have begun disappearing. The virus itself can be detected in isolated peripheral lymphocytes using an electron microscope, and viral DNA can be diagnosed using PCR. Immunological assays are used most frequently to diagnose bovine leukemia: gel immunodiffusion (ACID), immunoenzymatic assays (ELISA) as well as radioimmunological detection. These methods make use of antibodies against the antigenic proteins gp51 and p24.

BRIEF SUMMARY OF THE INVENTION

ELISA assays for diagnosing enzootic bovine leukemia are based on the determination of anti-BLV antibody levels in serum or milk. To construct the assay kit it is necessary to produce purified gp51 viral surface antigen. This antigen is produced in a culture of FLK cells infected with BLV, Cell cultures make frequent use of calf serum (FCS) containing bovine immunoglobulins that, despite tedious purification procedures, contaminate the resulting preparations with bovine antibodies, which leads to false positive results.

Available literature describes a series of labor-intensive methods of purifying the gp51 antigen, encompassing precipitation, extraction, centrifugation in a saccharose gradient, gel and ion exchange chromatography (Grunboeck M. et al., Polskie Archiwum Weterynaryjne 1986, 24, 327-336). Ukrainian patent (UA 68930 A) describes a culture medium containing avian serum (instead of bovine). The production of the purified antigen, however, requires the removal of a large quantity of ballasting avian antigens.

The unsolved problem in prior art are the difficult, tedious and expensive methods of purifying the antigen to be used in the ELISA assay. At the same time, due to the problems at this stage, contaminated antigen preparations are produced, which, when used in an ELISA assay, lead to erroneous results and make rapid and effective diagnostics of the disease impossible.

DETAILED DESCRIPTION OF THE INVENTION

The subject of the present invention is a method of obtaining pure BLV gp51 antigen characterized in that the antigen production process uses culture media totally devoid of bovine serum.

In a preferential embodiment of the present invention, culture media for FLK-BLV cells are used.

In the next preferential embodiment of the present invention, the culture media encompass HyQ® SFM4MegaVir™, HyQ® PF-Vero™, and Gibco® OptiPRO™ SFM.

The next subject of the present invention is the use of purified BLV gp51 antigen in a gel immunodiffusion assay or an ELISA assay.

The next subject of the present invention is a novel ELISA assay for detecting enzootic leukemia in cattle, characterized in that it contains a highly pure BLV gp51 BLV antigen obtained from cell culture media totally devoid of bovine serum.

An example embodiment of the present invention, which does not exhaust the scope of its protection, is given below.

EXAMPLE

FLK-BLV cells are cultured in dishes or culture flasks in DMEM medium without bovine serum, for example HyQ® SFM4MegaVir™, HyQ® PF-Vero™, and Gibco® OptiPRO™ SFM. The culture is maintained for 2-3 days until the cells reach a large density, and then for the subsequent several days, the medium is collected from above the cells and is maintained at −20° C. The collected medium is condensed 10-fold via ultrafiltration using an Amicon YM10 membrane and dialysed against 20 mM Tri-HCl pH 7.5, whereafter it is purified in a DEAE-Sepharose® FE column equilibrated with 20 mM TrisHCl pH 7.5 and eluted with a sodium chloride gradient (0-500 mM). Antigen gp51 containing fractions are pooled, dialysed against PBS and stored at −20 C.

The antigen thus obtained can be used in gel immunodiffusion assays or ELISA assays.

The invention claimed is:

1. A process for producing purified BLV gp51 antigen that is useful in an ELISA assay for diagnosing enzootic bovine leukemia comprising
   - i) culturing FLK-BLV cells in cell culture medium that is totally devoid of bovine serum, wherein the culture of FLK-BLV cells is maintained for 2 to 3 days, and wherein the FLK-BLV cells produce BLV gp51 antigen;
   - ii) collecting the medium from the above FLK-BLV cells containing the BLV gp51 antigen produced by the FLK-BLV cells;
   - iii) concentrating the BLV gp51 antigen in the medium at least 10-fold by ultra-filtration;
   - iv) dialyzing the condensed BLV gp51 antigen against 20 mM Tris-HCl pH 7.5; and
   - v) purifying the BLV gp51 antigen in a column comprising an anion exchange medium, wherein the BLV gp51 antigen is eluted from the column with a sodium chloride gradient.

2. The process of claim 1, further comprising the step of dialyzing the eluted BLV gp51 antigen of step v) against PBS.

3. The process of claim 1, wherein the sodium chloride gradient is 0 to 500 mM.

4. The process of claim 1, further comprising the step of maintaining the medium collected in step ii) at −20° C. prior to performing step iii).

5. The process of claim 1, wherein condensing the BLV gp51 antigen in step iii) comprises a membrane.

* * * * *